United States Patent
Chen et al.

(10) Patent No.: US 11,116,555 B2
(45) Date of Patent: Sep. 14, 2021

(54) WING-SHAPED ANGLE STEEL PLATE AND A BONE SHAFT FIXATION SYSTEM

(71) Applicant: Tianjin Zhengtian Medical Instrument Co., Ltd, Tianjin (CN)

(72) Inventors: Hua Chen, Beijing (CN); Peifu Tang, Beijing (CN)

(73) Assignee: TIANJIN ZHENGTIAN MEDICAL INSTRUMENT CO., LTD, Tianjin (CN)

( * ) Notice: Subject to any disclaimer, the term of this patent is extended or adjusted under 35 U.S.C. 154(b) by 146 days.

(21) Appl. No.: 16/343,152

(22) PCT Filed: Oct. 18, 2016

(86) PCT No.: PCT/CN2016/102447
§ 371 (c)(1),
(2) Date: Apr. 18, 2019

(87) PCT Pub. No.: WO2018/072100
PCT Pub. Date: Apr. 26, 2018

(65) Prior Publication Data
US 2019/0314066 A1    Oct. 17, 2019

(51) Int. Cl.
*A61B 17/80* (2006.01)
*A61B 17/86* (2006.01)
*A61B 17/00* (2006.01)

(52) U.S. Cl.
CPC ...... *A61B 17/8004* (2013.01); *A61B 17/8052* (2013.01); *A61B 17/864* (2013.01); *A61B 2017/00526* (2013.01)

(58) Field of Classification Search
CPC .. A61B 17/8085; A61B 17/80; A61B 17/8004
See application file for complete search history.

(56) References Cited

U.S. PATENT DOCUMENTS

| 5,352,228 A | 10/1994 | Kummer et al. |
| 2003/0069581 A1 | 4/2003 | Stinson et al. |
| 2013/0150853 A1* | 6/2013 | Blacklidge ......... A61B 17/8052 606/70 |

FOREIGN PATENT DOCUMENTS

| CN | 2074170 U | 4/1991 |
| CN | 2662843 Y | 12/2004 |
| CN | 201052174 Y | 4/2008 |

OTHER PUBLICATIONS

International Search Report (and its English translation) and Written Opinion for PCT Application No. PCT/CN2016/102447 filed Oct. 18, 2016, dated Jul. 21, 2017, 9 pages.

* cited by examiner

*Primary Examiner* — Andrew Yang
(74) *Attorney, Agent, or Firm* — Harness, Dickey & Pierce, P.L.C.; Anthony G. Fussner

(57) ABSTRACT

The present invention relates to a wing-shaped angle steel plate and a bone shaft fixation system. The wing-shaped angle steel plate comprises a wing fitting portion and a body fixation portion which are fixedly connected to each other. The wing fitting portion is used for supporting a fracture end and has a structure matched with an inner side surface of a bone shaft. The body fixation portion is used for fixing the wing fitting portion and has a structure matched with a front side of the bone shaft. The body fixation portion is provided with at least two first locking holes for passing through first locking screws at an intersection site with the wing fitting portion and is further provided with at least two second locking holes for passing through second locking screws in the structure matched with the front side of the bone shaft. In the wing-shaped angle steel plate, the wing fitting portion and the body fixation portion of the present invention are connected to each other and cooperate to fix and support the bone shaft fracture end site, and effectively ensure and help stable reduction and healing of the fracture sites.

16 Claims, 9 Drawing Sheets

WING-SHAPED ANGLE STEEL PLATE AND A BONE SHAFT FIXATION SYSTEM

This patent application is a U.S. national stage filing under 35 U.S.C. § 371 of International Application No. PCT/CN2016/102447 filed Oct. 18, 2016 (published as WO 2018/072100 on Apr. 26, 2018). The disclosure of the application identified in this paragraph is incorporated herein by reference in its entirety.

TECHNICAL FIELD

The present invention relates to the technical field of medical devices, and in particular, to a wing-shaped angle steel plate and a bone shaft fixation system used for non-union or fracture non-healing after a bone shaft fracture.

BACKGROUND TECHNIQUE

In the prior art, a bone fracture is divided into stable fracture and unstable fracture according to the degree of stability of the fracture end. For stable fracture, it usually was treated with manipulations and external fixation methods such as a plaster, a splint, a brace, or traction brake method, etc., are used to maintain stable fixation and achieve final healing; for unstable fracture, surgical treatment is required, including an internal fixation system and an external fixation system, and the internal fixation system is divided into a screw-plate fixation system and an intramedullary nail fixation system. However, regardless of which treatment method is adopted, large-sample follow-up studies have showed that some patients may suffer from fracture nonunion or delayed healing, with an incidence rate of up to 10%.

For patients suffering from fracture non-healing or delayed healing who are fixed by the screw-plate fixation system, besides the infection factors, these patients can be divided into two categories of multi-callus ones and few-callus ones according to the number of calluses formed at the fracture site; and can be divided into stable type and unstable type according to the degree of stability of fracture end. For patients with stable fracture end and multiple calluses, most of them can be treated by observation; while for patients with stable fracture end and few calluses, bone grafting treatment can be adopted. But for patients with unstable fracture, regardless of multiple calluses or few calluses, it is necessary to take various ways to strengthen the stability of the fracture end to promote the gradual healing of the fracture because of local instability of fracture. However, relying on the existing clinically available internal fixation methods, it is still impossible to perfectly solve the internal fixation problems such as defects of the fracture end, or unstable fracture end, non-healing or nonunion after comminuted fracture by adopting the screw-plate system for fixation (for example, nonunion 10 of a bone shaft 1 after fracture as shown in dotted round frame in FIG. 1), that is, there is no stable medical device designed specifically for nonunion and fracture non-healing. Therefore, it is urgent to develop an internal fixation apparatus, a system or a method for nonunion and non-healing after fracture.

SUMMARY OF THE INVENTION

To solve the problems of unstable fracture end, fracture non-healing or delayed healing occurring in the prior after the bone shaft fracture site is fixed using the screw-plate system, the present invention proposes a wing-shaped angle steel plate structure. By using a wing fitting portion and a body fixation portion that are connected and cooperated with each other and in close contact with a bone shaft, this wing-shaped angle steel plate can complete stable fixation of the fracture end and support the fracture end site of bone shaft internally, prevent dislocation of the fracture end and assist in the accurate positioning, reduction and healing of the fracture site. The present invention further relates to a bone shaft fixation system.

The technical solution of the present invention is as follows:

A wing-shaped angle steel plate, comprising a wing fitting portion and a body fixation portion, the wing fitting portion and the body fixation portion are fixedly connected to each other, the wing fitting portion is used for supporting a fracture end and has a structure matched with an inner side surface of a bone shaft, the body fixation portion is used for fixing the wing fitting portion and has a structure matched with a front side of the bone shaft, and the body fixation portion is provided with at least two first locking holes for passing through first locking screws at an intersection site with the wing fitting portion, and the first locking holes have angles such that the first locking screws passing therethrough can realize a close contact of the body fixation portion and the wing fitting portion with the bone shaft and realize a support to the inner side of the bone shaft, the body fixation portion is provided with at least two second locking holes for passing through a second locking screw on the structure matched with the front side of the bone shaft, and the second locking holes have angles such that the second locking screws passing therethrough can realize a close contact between the body fixation portion and the bone shaft and control rotation and axial stability of the body fixation portion.

The wing fitting portion has a structure that completely covers the fracture end.

The wing fitting portion has a structure that exposes the fracture end and supports the fracture end at a distal end and a proximal end of the fracture end, respectively.

The wing fitting portion and the body fixing portion are manufactured by an integral molding process.

The body fixing portion is further provided with at least two lateral compression holes for passing through a compression screw on the structure matched with the front side of the bone shaft, and the lateral compression holes have angles such that the compression screws passing therethrough generates pressures between the bone shaft and the wing-shaped angle steel plate.

The body fixation portion is provided with three second locking holes in the structure matched with the front side of the bone shaft, and the three second locking holes are arranged in line or in a triangle.

The body fixation portion is provided with more than four second locking holes in the structure matched with the front side of the bone shaft, and these second locking holes are arranged in line or in a polygon.

A bone shaft fixation system, comprising the foregoing wing-shaped angle steel plate, and further comprising first locking screws that pass through the first locking holes and second locking screws that pass through second locking holes for fixing the wing-shaped angle steel plate and a bone shaft lateral locking structure for fixing a fracture end, the bone shaft lateral locking structure comprises a locking steel plate and at least two third locking screws for fixing the locking steel plate, the locking steel plate having a structure matched with a lateral surface of the bone shaft, the locking steel plate is provided with at least two third locking holes for passing through the third locking screws in the structure matched with the bone shaft lateral surface, and each of the third locking screws passes through the corresponding third locking hole of the locking steel plate respectively.

The first locking screws and the second locking screws for fixing the wing-shaped angle steel plate have a diameter ranging from 2.4 to 4.5 mm.

The first locking screws and/or the second locking screws and/or the third locking screws are hollow locking screws or solid locking screws.

The technical effects of the present invention are as follows:

The present invention relates to a wing-shaped angle steel plate, comprising the wing fitting portion and the body fixation portion, the wing fitting portion and the body fixation portion are fixedly connected to each other and preferably can be formed integrally, the wing fitting portion is used for supporting the fracture end and has a structure matched with the inner side surface of the bone shaft, the body fixation portion is used for fixing the wing fitting portion and has a structure matched with the front side of the bone shaft, the body fixation portion is provided with at least two first locking holes for passing through the first locking screws at the intersection site with the wing fitting portion, and provided with at least two second locking holes for passing through the second locking screws are provided in the structure matched with the front side of the bone shaft. Each of the first locking holes and the second locking holes has respective specific angle to achieve a specific function in cooperation with the first locking screw and the second locking screw, respectively. In the wing-shaped angle steel plate, the wing fitting portion and the body fixation portion of the present invention are connected to each other and cooperate to fix and support the bone shaft fracture end site, thereby enhancing the stability of the fracture end and effectively ensuring and helping stable reduction and healing of the fracture site. The wing fitting portion and the body fixing portion with specific structures cooperate with the first locking holes provided with specific angles, such that the body locking portion and the wing fitting portion are in close contact with the bone shaft (i.e., the wing-shaped angle steel plate is tightly fitted with the bone shaft) after the first locking screws pass through along the direction of the first locking holes, and the support of the inner side of bone shaft can be achieved. The wing fitting portion and the body fixing portion with specific structures cooperate with the second locking holes provided with specific angles, such that a close contact of the body fixation portion with the bone shaft and control on rotation and axial stability of the body fixation portion can be achieved after the second locking screws pass through along the direction of the second locking holes. In addition, during actual uses, the first and second locking screws which can be minimally invasively implanted from the front side of the bone shaft and used to fix the wing-shaped angle steel plate are not interfered by the original fixation, especially the ingenious structure of the wing fitting portion solves the problem of minimal invasion inside the bone shaft that cannot be solved in the prior art. The incision is still made at the front side of the bone shaft, but the wing fitting portion can be extended into the inside of the bone shaft to support the fracture end, and support of the inner side of the bone shaft can be achieved through the cooperation of the first locking screw with the first locking hole provided with a specific angle, so as to further enhance the reliability of the fixation after the reduction and facilitate fracture healing.

For the wing-shaped angle steel plate proposed by the present invention, the wing fitting portion may preferably be of the structure that can completely cover the fracture end, or can be of the structure in which the fracture end is exposed and supported at a distal end and a proximal end, respectively. The specific shape and structure can be reasonably selected according to the fracture site, to cover the fracture end site, or expose the fracture end site, or cooperate with the fracture end site while supporting and stabilizing the fracture end, so as to accelerate and promote the fracture healing and achieve a better healing state.

The present invention further relates to a bone shaft fixation system comprising the foregoing wing-shaped angle steel plate and the first locking screws and the second locking screws, and further comprising a bone shaft lateral locking structure. The above components are used cooperatively. The wing-shaped angle steel plate can realize an effective support and fixation of the fracture end and a close contact with the bone shaft, the bone shaft lateral locking structure can achieve accurate positioning and fixation of the bone shaft fracture site using the locking steel plate, which further enhances the effective support and fixation after the bone shaft fracture and assists in the accurate positioning of the fracture site, thus effectively ensuring the stability of bone shaft after fracture reduction.

Figure 1:
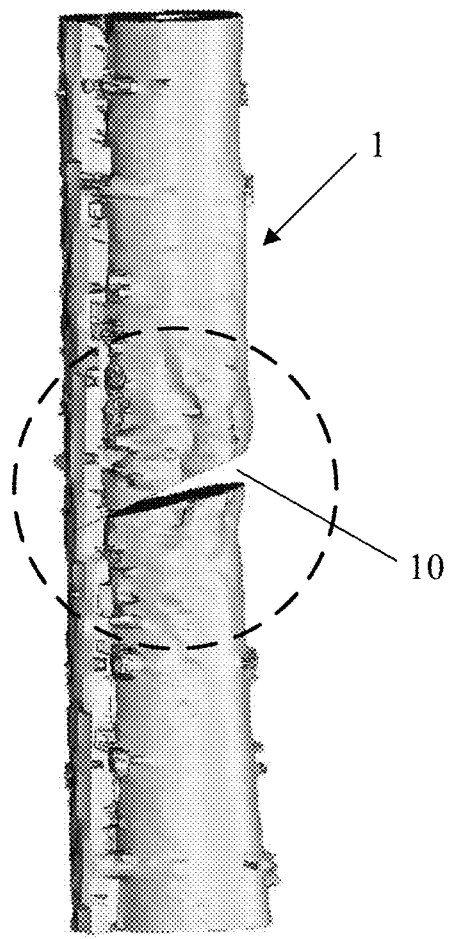
FIG. 1 is a schematic view of bone nonunion after a bone shaft fracture.

Reference numbers in the drawings are listed as follows: 1—bone shaft; 10—nonunion; 2—wing-shaped angle steel plate; 20—wing fitting portion; 21—body fixation portion; 2201—second locking hole; 2202—second locking hole; 2203—first locking hole; 2204—first locking hole; 2205—lateral compression hole; 2206—lateral compression hole; 2301—second locking screw; 2302—second locking screw; 2303—first locking screw; 2304—first locking screw; 2305—compression screw; 2306—compression screw; 2307—second locking screw; 2308—second locking screw; 3—bone shaft lateral locking structure; 30—locking steel plate.

DETAILED DESCRIPTION OF THE PREFERRED EMBODIMENTS

The present invention is further described with reference to the accompanying drawings.

The present invention relates to a wing-shaped angle steel plate, comprising a wing fitting portion and a body fixation portion, wherein the wing fitting portion and the body fixation portion are fixedly connected to each other. The wing fitting portion is used for supporting a fracture site (i.e. a fracture end) of the bone shaft and has a structure matched with an inner side surface of the bone shaft, and the body fixation portion is used for fixing the wing fitting portion and has a structure matched with a front side of the bone shaft. The body fixation portion is provided with at least two first locking holes for passing through first locking screws at an intersection site with the wing fitting portion, and the first locking holes have angles such that the first locking screws passing therethrough can realize a close contact with the bone shaft by the body fixation portion and the wing fitting portion and realize supporting of an inner side of the bone shaft, and the body fixation portion is provided with at least two second locking holes for passing through second locking screws in the structure matched with the front side of the bone shaft, the second locking holes have angles such that the second locking screws passing therethrough can realize a close contact between the body fixation portion and the bone shaft and control the rotation and axial stability of the body fixation portion. The specific structural shape of the wing fitting portion and the body fixing portion, the specific position of each locking hole and the number of locking holes can be reasonably set according to the practical applications and are not limited by the present invention and include but is not limited to the above range. For example, the wing fitting portion can be designed into a structure that completely covers the non-healing or nonunion sites of the fracture end, or can be designed into a structure that exposes the non-healing or nonunion sites of the fracture end. For another example, the body fixation portion is provided with three second locking holes in a structure matched with the front side of the bone shaft, and the three second locking holes are arranged in line or in a triangle; or the body fixation portion is provided with four or more second locking holes in the structure matched with the front side of the bone shaft, and these second locking holes are arranged in line or in a polygon. In other words, in the present invention, the length of the wing-shaped angle steel plate can be determined by the number of locking holes provided in a structure of the body fixation portion matched with the front side of the bone shaft, for example, the length of the wing-shaped angle steel plate may be such that four holes, six holes or eight holes are provided.

Figure 2:
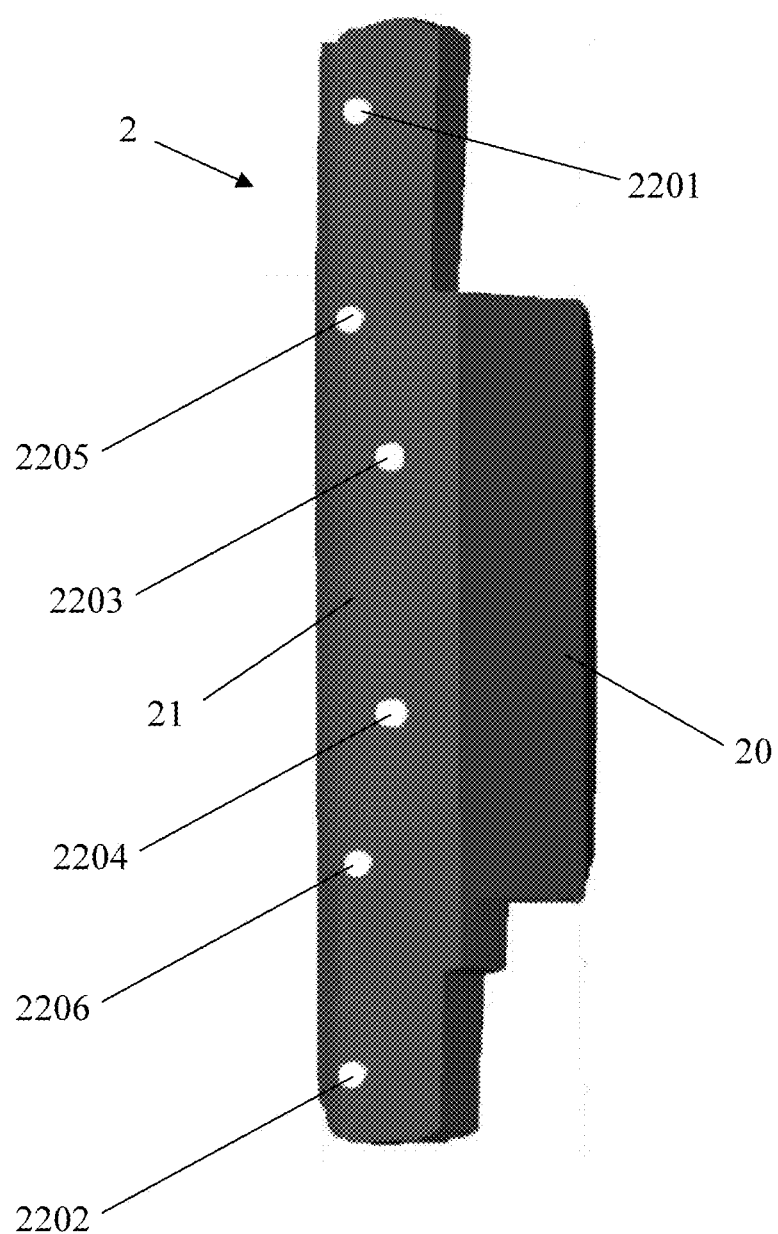
FIG. 2 is a front view of a first preferred structure of the wing-shaped angle steel plate of the present invention.

FIG. 2 is a front view of a first preferred structure of a wing-shaped angle steel plate 2 of the present invention. As shown in FIG. 2, a wing-shaped angle steel plate, comprising the wing fitting portion 20 and the body fixation portion 21. The wing fitting portion 20 and the body fixation portion 21 are fixedly connected to each other, the wing fitting portion 20 and the body fixing portion 21 are preferably made of a stainless steel by an integrated molding process. The wing fitting portion 20 is used for supporting and stabilizing a bone shaft fracture site and has a structure matched with an inner side surface of the bone shaft, and the wing fitting portion 20 has a structure that completely covers bone shaft fracture sites, i.e. the non-healing or nonunion sites of fracture end, to support and stabilize the fracture end and promote fracture healing. The body fixation portion 21 is used for fixing the wing fitting portion 20 and has a structure matched with the front side of the bone shaft, the body fixation portion 21 is provided with two first locking holes (for example, reference numerals 2203 and 2204, i.e. the first locking hole 2203 and first locking hole 2204) for passing through first locking screws at the intersection site with the wing fitting portion 20. When the first locking screws are used for fixation, the fixation of the wing fitting portion 20, a close contact of the body fixation portion 21 and the wing fitting portion 20 with the bone shaft, and the supporting of the inner side of the bone shaft are achieved. The body fixation portion 21 is provided with two second locking holes (for example, reference numerals 2201 and 2202, i.e. the second locking hole 2201 and the second locking hole 2202) for passing through second locking screws in the structure matched with the front side of the bone shaft. When the second locking screws are used for fixation, the axial support, fixation, anti-rotation of the body fixation portion 21 and the tight fit to the front side of the bone shaft are achieved. The body fixing portion 21 is further provided with two lateral compression holes (for example, reference numerals 2205 and 2206, i.e. the lateral compression hole 2205 and the lateral compression hole 2206) for passing through compression screws in the structure matched with the front side of the bone shaft. When the compression screw is used for lateral locking at an angle, a pressure can be generated between the bone shaft and the wing-shaped angle steel plate to further strengthen the tight fit between the wing fitting portion 20 and the inner side of the bone shaft and the tight fit between the body fixation portion 21 and the front side of the bone shaft, that is, to achieve the close contact/tight fit between the wing-shaped angle steel plate 2 and the long bone shaft. In addition, as shown in FIG. 2, the second locking hole 2201, the second locking hole 2202, the lateral compression hole 2205 and the lateral compression hole 2206 are arranged in an approximately straight line, and can be arbitrarily arranged in any shape as long as an effective fixation and minimum injury to patients can be guaranteed during actual use. In the present invention, the wing-shaped angle steel plate 2 adopts an integrally formed structure of a body fixation portion 21 and a wing fitting portion 20, and the wing fitting portion 20 is of the structure matched with the inner side of the bone shaft, which can achieve good stability and support of the non-healing or nonunion sites of the fracture end, assist in the accurate positioning of the fracture site, and effectively ensure the stability of bone healing. The body fixation portion 21 is of the structure matched with the front side of the bone shaft, which can achieve axial positioning and fixation of the fracture area of the long bone shaft, prevent dislocation of the fracture site with good adhesion and fixation, to further guarantee and help accurate positioning, reduction and healing of the fracture sites.

Figure 3:
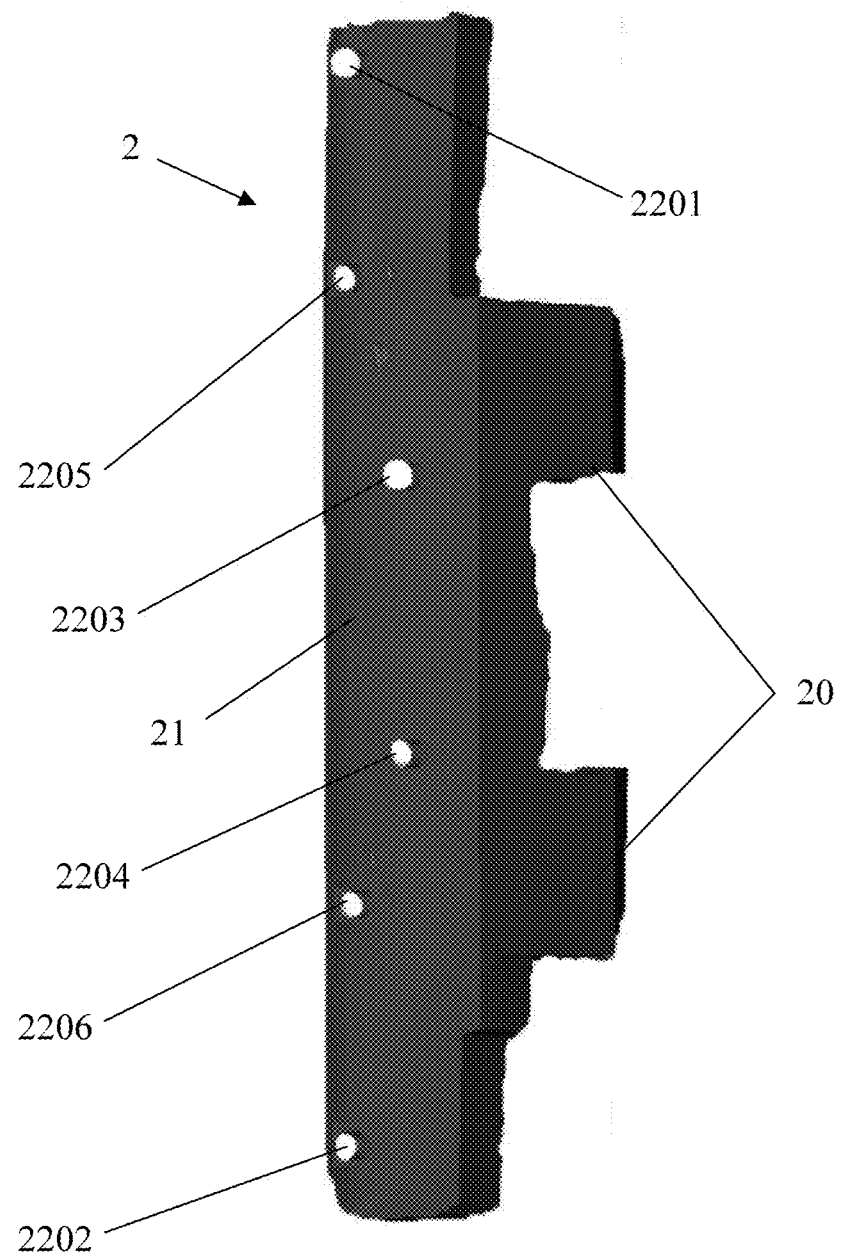
FIG. 3 is a front view of a second preferred structure of the wing-shaped angle steel plate of the present invention.
Figure 4:
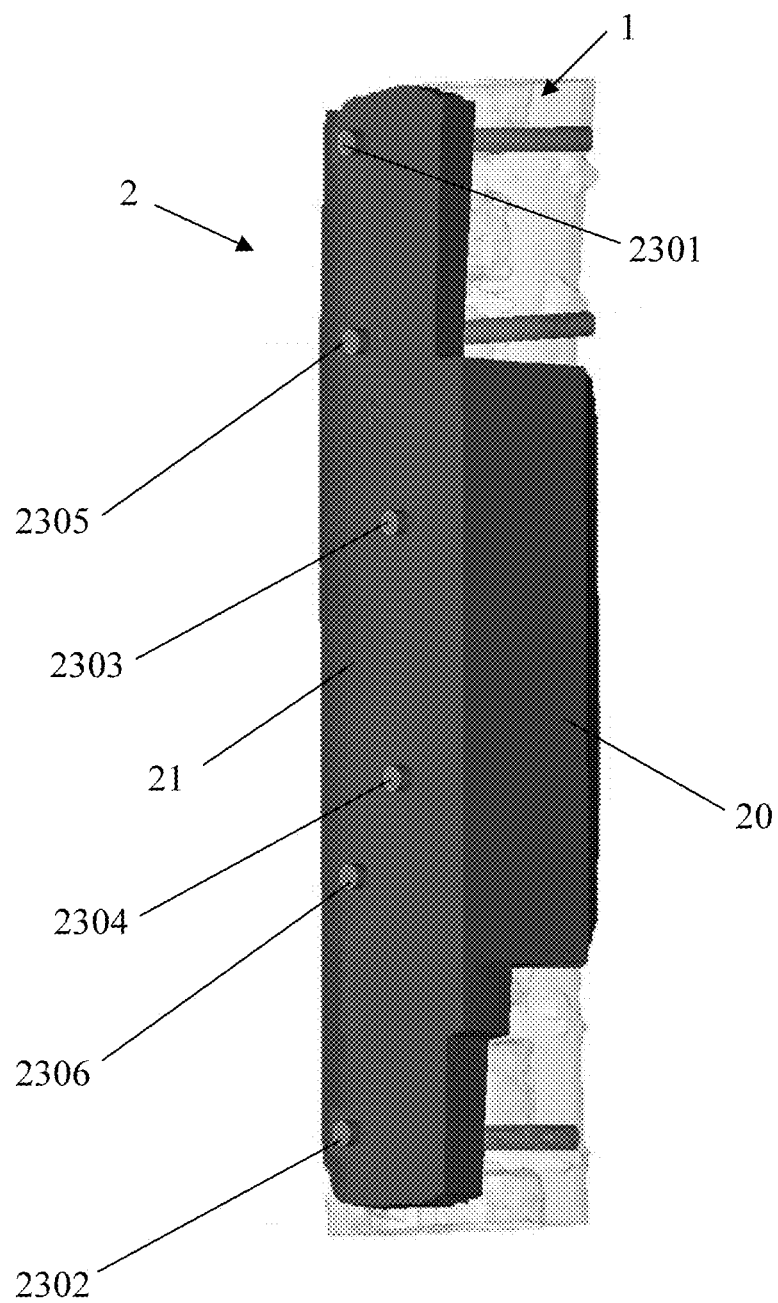
FIG. 4 is a schematic structural view showing a first preferred wing-shaped angle steel plate of the present invention in a used state.
Figure 5:
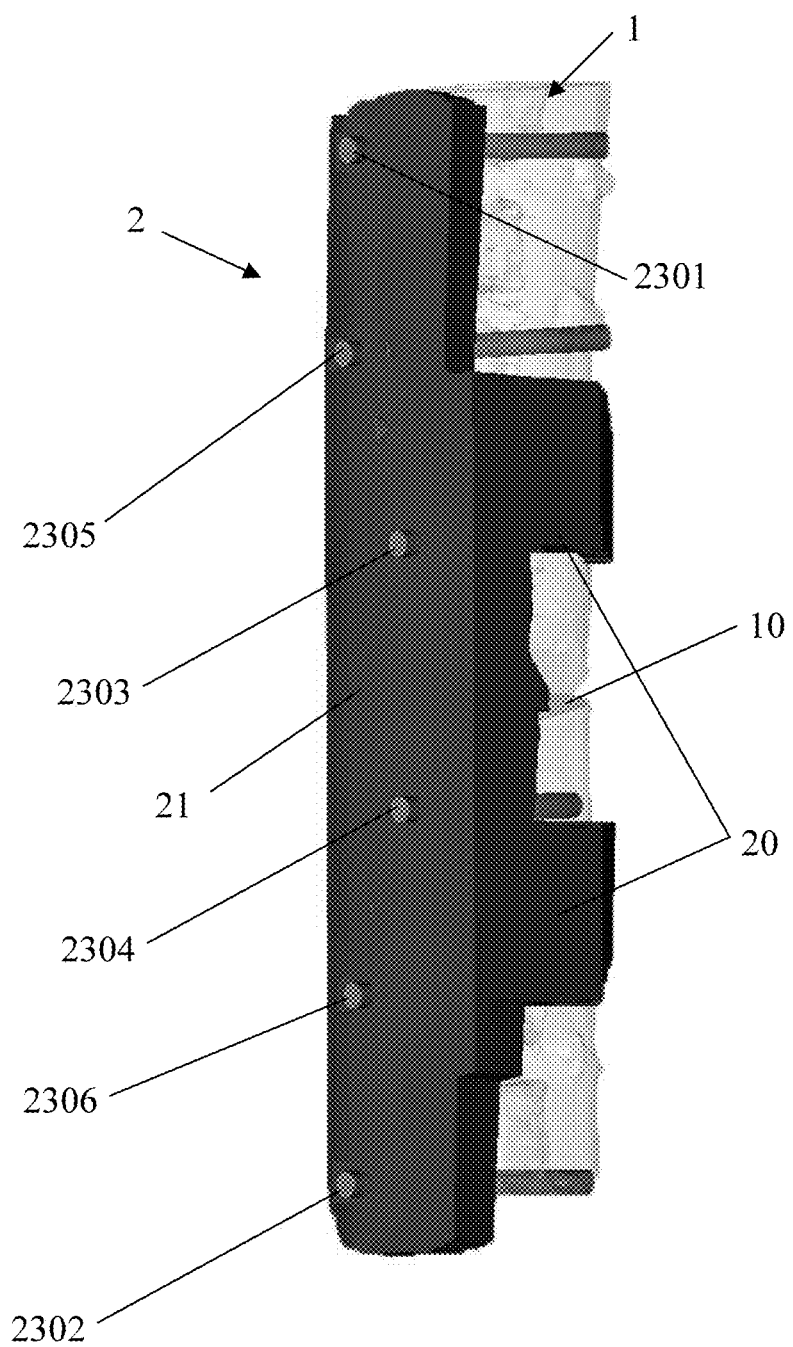
FIG. 5 is a schematic structural view showing a second preferred wing-shaped angle steel plate of the present invention in a used state.
Figure 6:
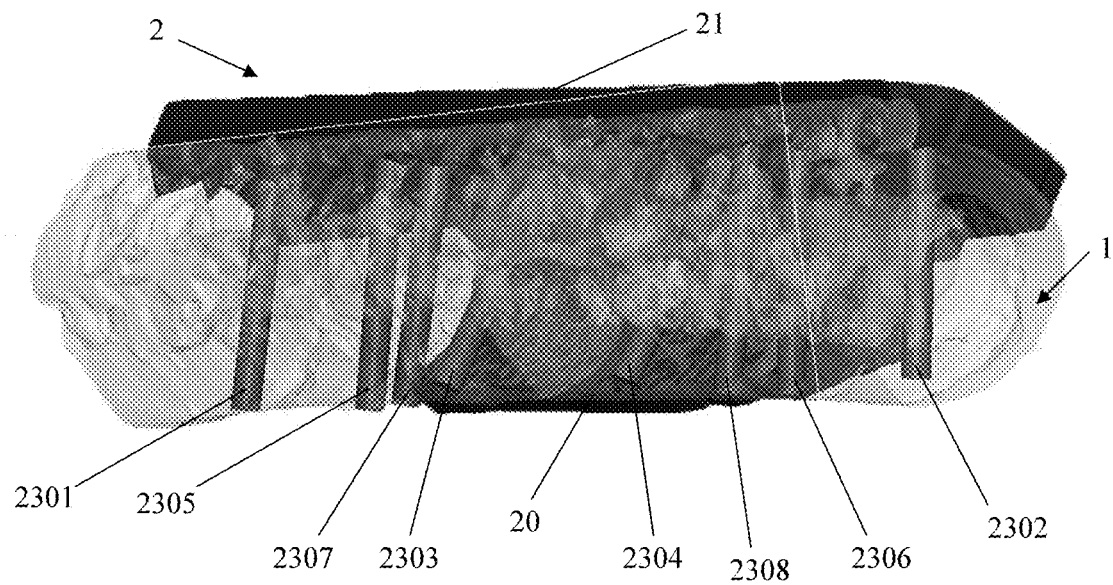
FIG. 6 is a schematic structural view showing a third preferred wing-shaped angle steel plate of the present invention in a used state.
Figure 7:
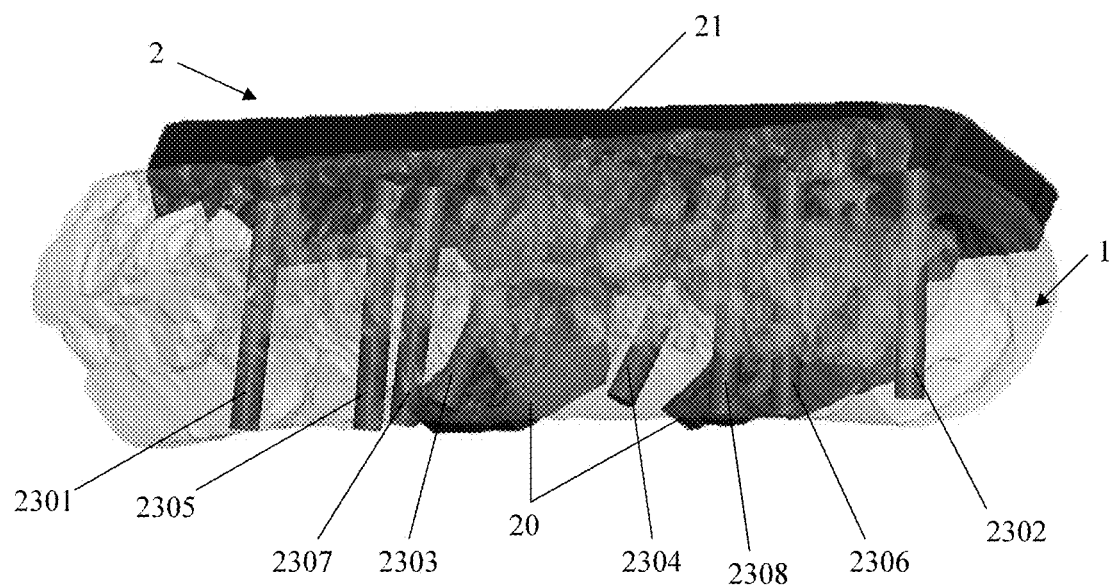
FIG. 7 is a schematic structural view showing a fourth preferred wing-shaped angle steel plate of the present invention in a used state.

FIG. 3 is a front view of a second preferred structure of the wing-shaped angle steel plate 2 of the present invention. As shown in FIG. 3, the wing-shaped angle steel plate 2 also comprises a wing fitting portion 20 and a body fixation portion 21 which are fixedly connected to each other and provided with specific structures. In this embodiment, except for the wing fitting portion 20, other components and functions thereof are the same as those shown in FIG. 2. The wing fitting portion 20 is still used for supporting the fracture end and has a structure matched with the inner side surface of the bone shaft. The difference from the embodiment shown in FIG. 2 is that the wing fitting portion 20 shown in FIG. 3 has a structure that exposes the non-healing or nonunion sites of the fracture end and supports the fracture end at the distal end and the proximal end of the non-healing or nonunion sites of the fracture end respectively, to expose the fracture end portion and accelerate and promote the fracture healing and achieve a better fracture healing state while supporting and stabilizing the fracture end.

Figure 8:
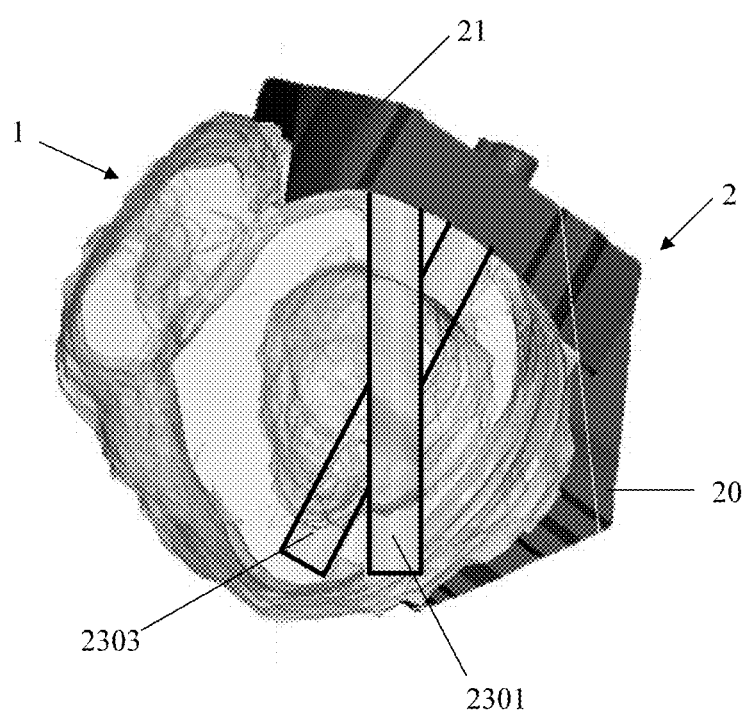
FIG. 8 is a side view of FIG. 6 or FIG. 7.

The working principle and use method of the wing-shaped angle steel plate 2 proposed by the present invention are specifically described as follows:

The schematic structural views showing a preferred wing-shaped angle steel plate of the present invention in a used state are shown in FIG. 4 to FIG. 8. In actual uses, first, in the fracture site, for example, in the front side of the bone shaft 1, that is the front side of the nonunion site, the skin, subcutaneous, quadriceps femoris muscle belly and periosteum are cut along long axis of limb, to expose the nonunion site, and then cortical bone cutting is performed at the nonunion site using a sharp bone knife, to fully expose the nonunion site; then a slot is made at the nonunion site using a Kirschner wire and a bone knife, and then a medullary cavity is reperfused along the medullary cavity with the Kirschner wire; the bone cement and structural bone graft are respectively taken by the minimally-invasive bone drill; the bone cement is filled into the nonunion site, and the structural bone graft is embedded in the medullary cavity of the nonunion site; and backfilling is performed with the slotted bone. A submucosal dissection is performed using the extensibility of the skin and muscle, then the wing-shaped angle steel plate 2 as shown in FIG. 2 or FIG. 3 is implanted under the periosteum. The body fixation portion 21 is implanted at the front side of the bone shaft and the wing fitting portion 20 is extended into the inside of the bone shaft to protect the fracture end, and the inner side of the wing fitting portion 20 is in close contact with the inner side of the bone shaft to play a good supporting role. The embodiment shown in FIG. 4 and FIG. 6 employs the wing-shaped angle steel plate 2 having a wing fitting portion 20 structure that completely covers the fracture end as shown in FIG. 2. The embodiment shown in FIG. 5 and FIG. 7 employs the wing-shaped angle steel plate 2 having a wing fitting portion 20 structure that exposes the fracture end and supports the fracture end at the distal end and the proximal end of the fracture end as shown in FIG. 3. The inner side of the body fixation portion 21 closely contacts and fits with the front side of the bone shaft to play a stable anti-rotation and fixation role. The wing fitting portion 20 and the body fixation portion 21 cooperate with each other to perfectly achieve effective internal support and fixation for the bone shaft fracture, assist in accurate positioning and healing of the fracture site, and effectively ensure the stability of reduction and healing after bone shaft fracture. As shown in FIG. 4 to FIG. 7, the first locking screw 2303 and the first locking screw 2304 respectively pass through the first locking holes 2203 and first locking hole 2204 provided in the body fixation portion 21 at the intersection site with the wing fitting portion 20, to realize the fixation of the wing fitting portion 20, the close contact of the body fixation portion 21 and the wing fitting portion 20 with the bone shaft and the support of the inner side of the bone shaft. The second locking screw 2301 and the second locking screw 2302 respectively pass through the second locking hole 2201 and the second locking hole 2202 provided in the structure of the body fixation portion 21 matched with the front side of the bone shaft, to achieve axial support, fixation, anti-rotation of the body fixation portion 21 and the tight fit with the front side of the bone shaft. Referring to the embodiments shown in FIG. 6 and FIG. 7 (FIG. 8 is a side view of FIG. 6 or FIG. 7), four second locking holes and four second locking screws are provided, that is, in addition to the second locking screw 2301 and the second locking screw 2302, a second locking screw 2307 and a second locking screw 2308 are provided. The four second locking screws can be arranged in a line or in a polygon, to further strengthen axial support, fixation, anti-rotation and fitting effects of the body fixation portion 21. In addition, the compression screw 2305 and the compression screw 2306 respectively pass through a lateral compression hole 2205 and a lateral compression hole 2206 provided in the structure of the body fixation portion matched with the front side of the bone shaft, and the lateral compression hole has an angle such that the compression screw passing therethrough generates a pressure between the bone shaft and the wing-shaped angle steel plate, as shown in FIG. 4 to FIG. 7, to further enhance the tight fit of the wing fitting portion 20 to the inner side of the bone shaft and the close contact/fit between the body fixation portion 21 and the front side of the bone shaft, that is, the close contact/tight fit between the wing-shaped angle steel plate 2 and the long bone shaft. After fixation and support by the wing-shaped angle steel plate 2 of the present invention, a negative pressure drainage tube is intubated, and periosteum, myofascial fascia, deep fascia, subcutaneous tissue and skin are closed by suture. The drainage tube is pulled out 48 hours after the operation. In addition, the patient with fracture takes daily exercises of passive extreme knee motion, lower limb isometric contraction, and weight-bearing activities under pain tolerance (toes on ground by 5 kg). The patient receives x-ray examination monthly to determine the weight-bearing process according to fracture healing condition until the patient fully recovers.

The present invention further relates to a bone shaft fixation system, comprising the foregoing wing-shaped angle steel plate, at least four locking screws for fixing the wing-shaped angle steel plate (at least two first locking screws passing through the first locking holes and at least two second locking screws passing through the second locking holes), and a bone shaft lateral locking structure for fixing a fracture end, wherein the structure of the wing-shaped angle steel plate is shown in FIGS. 2-8. The bone shaft lateral locking structure comprises a locking steel plate and at least two third locking screws for fixing the locking steel plate, and the locking steel plate has a structure matched with the bone shaft lateral surface. The locking steel plate is provided with at least two third locking holes for passing through the third locking screws in the structure matched with the bone shaft lateral surface, and each of the third locking screws passes through the third locking holes of the locking steel plate.

Preferably, the locking screws (the first locking screws and the second locking screws) for fixing the wing-shaped angle steel plate have a diameter ranging from 2.4 to 4.5 mm. The locking screws (the first locking screws and the second locking screws) for fixing the wing-shaped angle steel plate and the locking screws (the third locking screws) for fixing the locking steel plate are hollow locking screws or solid locking screws.

Figure 9:
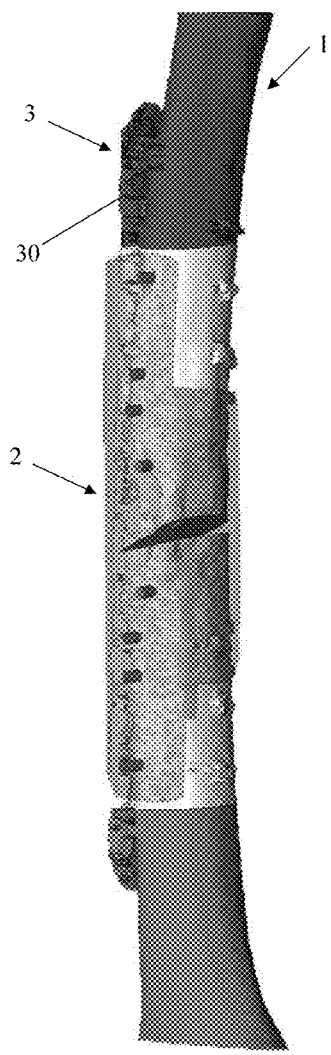
FIG. 9 is a structural front view showing one preferred bone shaft fixation system of the present invention in a used state.
Figure 10:
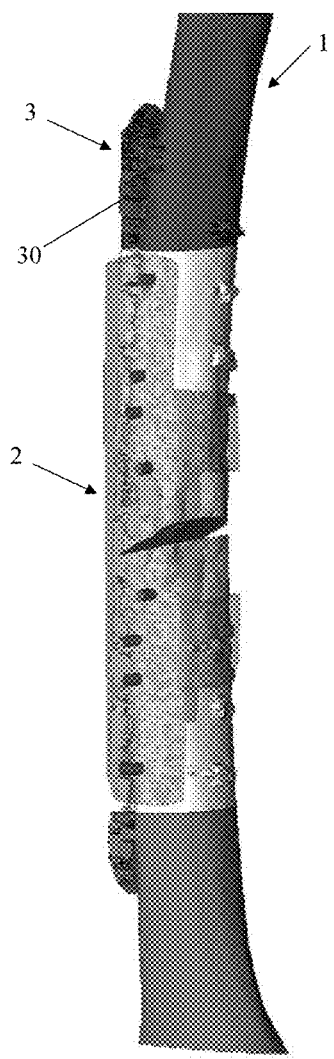
FIG. 10 is a structural front view showing another preferred bone shaft fixation system of the present invention in a used state.

According to the schematic structural views showing a preferred bone shaft fixation system in a used state in FIG. 9 and FIG. 10, the bone shaft fixation system comprises a wing-shaped angle steel plate 2 and a bone shaft lateral locking structure 3 shown in FIG. 2 or FIG. 3. The wing-shaped angle steel plate 2 shown in FIG. 9 has a wing fitting portion 20 that completely covers the fracture end as shown in FIG. 2, and the wing-shaped angle steel plate 2 shown in FIG. 10 has a wing fitting portion 20 structure that exposes a fracture end and supports the fracture end at the distal end and the proximal end of the fracture end as shown in FIG. 3. A plurality of locking screws as shown in FIGS. 4-8 as described above are used for fixing the wing-shaped angle steel plate 2. The bone shaft lateral locking structure 3 comprises a locking steel plate 30 and a third locking screw for fixing the locking steel plate 30. Preferably, the locking steel plate 30 is preferably of a simple rectangular structure, and the locking steel plate 30 has a structure matched with the bone shaft lateral surface. The locking steel plate 30 is provided with a plurality of openings (third locking holes) in the structure matched with the bone shaft lateral surface. A plurality of third locking screws for fixing the locking steel plate 30 may be set in correspondence to the number of openings in the locking steel plate 30, and the locking screws may be arranged in parallel, or some or all of them may be arranged in an angle. The third locking screws may be hollow locking screws or solid locking screws. The number of screws, the arrangement shape of screws and the angle between the screw and the locking steel plate 30 can be set according to actual needs, as long as effective fixation can be guaranteed, that is, each locking screws is subjected to different stress by reasonable layout, to achieve and help accurate positioning and stable reduction and fixation of the fracture sites, maximize the optimal fixation stability and ensure minimum injury to patients during actual applications.

The working principle and use method of the bone shaft fixation system proposed by the present invention are specifically described as follows:

As shown in FIG. 9 and FIG. 10, the bone shaft fixation system proposed by the present invention can be fully implanted from a conventional anterolateral incision, that is, the bone shaft lateral locking structure 3 and the wing-shaped angle steel plate 2 can be implanted together from the same conventional anterolateral incision. Thus, only one incision is required to achieve the implantation of the bone shaft fixation system of the present invention, the intraoperative injury, degree of injury and amount of bleeding are usually smaller, and the postoperative healing and recovery speed are faster. The working principle and use method of the wing-shaped angle steel plate 2 shown in FIGS. 2-8 are the same as those described above. In addition, the bone shaft lateral locking structure 3 is a locking steel plate 30 structure, and the locking steel plate 30 is in close contact with the bone shaft lateral surface. Several third locking screws pass through the openings of the locking steel plate 30 to enter from the bone shaft lateral surface and traverse the bone shaft to fix the fracture end. The bone shaft lateral locking structure 3 cooperates with the wing-shaped angle steel plate 2 to further strengthen the effective support and fixation after bone shaft fracture and assist in the accurate positioning of the fracture sites, thereby effectively ensuring the stability after reduction of the bone shaft fracture.

It should be noted that the foregoing described specific embodiments may enable those skilled in the art to more fully understand the present invention rather than limit the invention in any way. Therefore, although the present invention has been described in detail with reference to the drawings and embodiments, those skilled in the art should understand that modifications or equivalent replacements may be made to the present invention. In short, all technical solutions and improvements made without departing from the concepts and scope of the present invention shall fall within the scope of protection of the present invention.

The invention claimed is:

1. A wing-shaped angle steel plate, comprising a wing fitting portion and a body fixation portion, the wing fitting portion and the body fixation portion are fixedly connected to each other, the wing fitting portion is used for supporting a fracture end and has a structure matched with an inner side surface of a bone shaft, the body fixation portion is used for fixing the wing fitting portion and has a structure matched with a front side of the bone shaft, and the body fixation portion is provided with at least two first locking holes for passing through first locking screws at an intersection site with the wing fitting portion, and the first locking holes have angles such that the first locking screws passing therethrough can realize a close contact of the body fixation portion and the wing fitting portion with the bone shaft and realize a support to the inner side of the bone shaft, the body fixation portion is provided with at least two second locking holes for passing through a second locking screw on the structure matched with the front side of the bone shaft, and the second locking holes have angles such that the second locking screws passing therethrough can realize a close contact between the body fixation portion and the bone shaft and control rotation and axial stability of the body fixation portion; wherein the body fixing portion is further provided with at least two lateral compression holes for passing through a compression screw on the structure matched with the front side of the bone shaft, and the lateral compression holes have angles such that the compression screws passing therethrough generates pressures between the bone shaft and the wing-shaped angle steel plate.

2. The wing-shaped angle steel plate according to claim 1, wherein the wing fitting portion has a structure that completely covers the fracture end.

3. The wing-shaped angle steel plate according to claim 2, wherein the body fixation portion is provided with three second locking holes in the structure matched with the front side of the bone shaft, and the three second locking holes are arranged in line or in a triangle.

4. The wing-shaped angle steel plate according to claim 2, wherein the body fixation portion is provided with more than four second locking holes in the structure matched with the front side of the bone shaft, and these second locking holes are arranged in line or in a polygon.

5. The wing-shaped angle steel plate according to claim 1, wherein the wing fitting portion has a structure that exposes the fracture end and supports the fracture end at a distal end and a proximal end of the fracture end, respectively.

6. The wing-shaped angle steel plate according to claim 5, wherein the body fixation portion is provided with three second locking holes in the structure matched with the front side of the bone shaft, and the three second locking holes are arranged in line or in a triangle.

7. The wing-shaped angle steel plate according to claim 5, wherein the body fixation portion is provided with more than four second locking holes in the structure matched with the front side of the bone shaft, and these second locking holes are arranged in line or in a polygon.

8. The wing-shaped angle steel plate according to claim 1, wherein the wing fitting portion and the body fixing portion are manufactured by an integral molding process.

9. The wing-shaped angle steel plate according to claim 8, wherein the body fixation portion is provided with three second locking holes in the structure matched with the front side of the bone shaft, and the three second locking holes are arranged in line or in a triangle.

10. The wing-shaped angle steel plate according to claim 8, wherein the body fixation portion is provided with more than four second locking holes in the structure matched with the front side of the bone shaft, and these second locking holes are arranged in line or in a polygon.

11. The wing-shaped angle steel plate according to claim 1, wherein the body fixation portion is provided with three second locking holes in the structure matched with the front side of the bone shaft, and the three second locking holes are arranged in line or in a triangle.

12. The wing-shaped angle steel plate according to claim 1, wherein the body fixation portion is provided with more than four second locking holes in the structure matched with the front side of the bone shaft, and these second locking holes are arranged in line or in a polygon.

13. A bone shaft fixation system, comprising a wing-shaped angle steel plate that comprises a wing fitting portion and a body fixation portion, the wing fitting portion and the body fixation portion are fixedly connected to each other, the wing fitting portion is used for supporting a fracture end and has a structure matched with an inner side surface of a bone shaft, the body fixation portion is used for fixing the wing fitting portion and has a structure matched with a front side of the bone shaft, and the body fixation portion is provided with at least two first locking holes for passing through first locking screws at an intersection site with the wing fitting portion, and the first locking holes have angles such that the first locking screws passing therethrough can realize a close contact of the body fixation portion and the wing fitting portion with the bone shaft and realize a support to the inner side of the bone shaft, the body fixation portion is provided with at least two second locking holes for passing through a second locking screw on the structure matched with the front side of the bone shaft, and the second locking holes have angles such that the second locking screws passing therethrough can realize a close contact between the body fixation portion and the bone shaft and control rotation and axial stability of the body fixation portion;

the bone shaft fixation system further comprising first locking screws that pass through the first locking holes and second locking screws that pass through second locking holes for fixing the wing-shaped angle steel plate and a bone shaft lateral locking structure for fixing a fracture end, the bone shaft lateral locking structure comprises a locking steel plate and at least two third locking screws for fixing the locking steel plate, the locking steel plate having a structure matched with a lateral surface of the bone shaft, the locking steel plate is provided with at least two third locking holes for passing through the third locking screws in the structure matched with the bone shaft lateral surface, and each of the third locking screws passes through the corresponding third locking hole of the locking steel plate respectively.

14. The bone shaft fixation system according to claim 13, wherein the first locking screws and the second locking screws for fixing the wing-shaped angle steel plate have a diameter ranging from 2.4 to 4.5 mm.

15. The bone shaft fixation system according to claim 14, wherein the first locking screws and/or the second locking screws and/or the third locking screws are hollow locking screws or solid locking screws.

16. The bone shaft fixation system according to claim 13, wherein the first locking screws and/or the second locking screws and/or the third locking screws are hollow locking screws or solid locking screws.

* * * * *